(12) United States Patent
Park et al.

(10) Patent No.: US 9,492,809 B2
(45) Date of Patent: Nov. 15, 2016

(54) CARBON OXIDES CONVERSION PROCESS

(75) Inventors: Colin William Park, Darlington (GB); Brian Peter Williams, Stockton on Tees (GB); Graeme Douglas Campbell, Clitheroe (GB); David Allan Buckworth, Middlesbrough (GB)

(73) Assignee: Johnson Matthey PLC, London (GB)

( * ) Notice: Subject to any disclaimer, the term of this patent is extended or adjusted under 35 U.S.C. 154(b) by 1300 days.

(21) Appl. No.: 13/378,589

(22) PCT Filed: May 24, 2010

(86) PCT No.: PCT/GB2010/050843
§ 371 (c)(1),
(2), (4) Date: Mar. 19, 2012

(87) PCT Pub. No.: WO2010/146379
PCT Pub. Date: Dec. 23, 2010

(65) Prior Publication Data
US 2012/0202681 A1    Aug. 9, 2012

(30) Foreign Application Priority Data
Jun. 17, 2009 (GB) .................................. 0910364.9

(51) Int. Cl.
| | | |
|---|---|---|
| *B01J 21/00* | (2006.01) | |
| *B01J 23/00* | (2006.01) | |
| *B01J 25/00* | (2006.01) | |
| *B01J 29/00* | (2006.01) | |
| *B01J 23/70* | (2006.01) | |
| *B01J 23/72* | (2006.01) | |
| *B01J 21/04* | (2006.01) | |
| *B01J 23/80* | (2006.01) | |
| *B01J 35/00* | (2006.01) | |
| *B01J 35/02* | (2006.01) | |
| *B01J 37/00* | (2006.01) | |
| *B01J 37/12* | (2006.01) | |
| *B01J 37/18* | (2006.01) | |
| *C01B 3/16* | (2006.01) | |
| *C07C 29/154* | (2006.01) | |

(52) U.S. Cl.
CPC .................. *B01J 21/04* (2013.01); *B01J 23/80* (2013.01); *B01J 35/0026* (2013.01); *B01J 35/0053* (2013.01); *B01J 35/023* (2013.01); *B01J 37/0045* (2013.01); *B01J 37/12* (2013.01); *B01J 37/18* (2013.01); *C01B 3/16* (2013.01); *C07C 29/154* (2013.01); *Y02P 20/52* (2015.11)

(58) Field of Classification Search
USPC ....... 502/244, 342, 307, 324, 346, 100, 300, 502/344, 345
See application file for complete search history.

(56) References Cited

U.S. PATENT DOCUMENTS

| | | | | |
|---|---|---|---|---|
| 4,256,682 A | * | 3/1981 | Denton | ..................... B01J 21/08 423/338 |
| 4,441,927 A | * | 4/1984 | Getz | ....................... C22C 1/045 419/33 |
| 4,535,071 A | | 8/1985 | Schneider et al. | |
| 4,863,894 A | | 9/1989 | Chinchen et al. | |
| 5,972,207 A | * | 10/1999 | Johns | ..................... C10G 35/09 208/137 |
| 6,919,066 B2 | | 7/2005 | Hölzle et al. | |
| 7,387,983 B2 | * | 6/2008 | Holzle | ..................... B01J 23/80 502/326 |
| 2008/0033218 A1 | | 2/2008 | Lattner et al. | |

FOREIGN PATENT DOCUMENTS

| | | |
|---|---|---|
| EP | 0 125 689 A2 | 11/1984 |
| EP | 0 157 480 A2 | 10/1985 |
| EP | 0 202 824 A2 | 11/1986 |
| EP | 0 217 513 A1 | 4/1987 |
| EP | 0 296 734 A1 | 12/1988 |
| GB | 1010871 | 11/1965 |
| GB | 1159035 | 7/1969 |
| GB | 1 296 212 | 11/1972 |
| GB | 1 405 012 | 9/1975 |
| WO | WO-2008/047166 A2 | 4/2008 |
| WO | WO-2008/146032 A1 | 12/2008 |

OTHER PUBLICATIONS

Evans et al., "On the Determination of Copper Surface Area by Reaction with Nitrous Oxide," *Applied Catalysis*, 1983, vol. 7, pp. 75-83.
International Search Report dated Sep. 28, 2010, from International Application No. PCT/GB2010/050843.
International Preliminary Report on Patentability dated Dec. 20, 2011, from International Application No. PCT/GB2010/050843.

* cited by examiner

*Primary Examiner* — James McDonough
(74) *Attorney, Agent, or Firm* — RatnerPrestia

(57) ABSTRACT

A carbon oxides conversion process includes reacting a carbon oxide containing process gas containing hydrogen and/or steam and containing at least one of hydrogen and carbon monoxide in the presence of a catalyst including shaped units formed from a reduced and passivated catalyst powder, the powder including copper in the range 10-80% by weight, zinc oxide in the range 20-90% by weight, alumina in the range 5-60% by weight and optionally one or more oxidic promoter compounds selected from compounds of Mg, Cr, Mn, V, Ti, Zr, Ta, Mo, W, Si and rare earths in the range 0.01-10% by weight, wherein said shaped units have a reduced to as-made mean horizontal crush strength ratio of $\geq 0.5:1$ and a copper surface area above 60 $m^2/g$ Cu.

16 Claims, No Drawings

CARBON OXIDES CONVERSION PROCESS

CROSS-REFERENCE TO RELATED APPLICATIONS

This application is the U.S. National Phase application of PCT International Application No. PCT/GB2010/050843, filed May 24, 2010, and claims priority of British Patent Application No. 0910364.9, filed Jun. 17, 2009, the disclosures of both of which are incorporated herein by reference in their entireties for all purposes.

FIELD OF THE INVENTION

This invention relates to carbon oxide conversion reactions such as the water-gas shift reaction and methanol synthesis, and copper-containing catalysts suitable for use in such reactions.

BACKGROUND OF THE INVENTION

Carbon oxide conversion processes are of considerable importance in the manipulation of synthesis gas by the water-gas shift reaction and the production of alcohols such as methanol. These reactions are depicted below.

$$CO + H_2O \rightarrow CO_2 + H_2$$

$$CO + 2H_2 \rightarrow CH_3OH$$

$$CO_2 + 3H_2 \rightarrow CH_3OH + H_2O$$

The catalysts for such reactions are generally produced by forming into pellets small discrete particles of an intimate mixture of copper oxide and one or more other oxidic materials, generally including zinc oxide, that are not reduced under the conversion reaction process conditions. The intimate mixture is generally made by precipitation of copper compounds and compounds convertible to the other oxidic materials, and/or precipitation of the copper compounds in the presence of the other oxidic materials or compounds convertible thereto, followed by calcination to convert the precipitated copper compounds, and other components as necessary, to the oxides. Hence pellets are formed form oxidic powders. In order to generate the active catalyst, the pellets are subjected to reducing conditions to reduce the copper oxide in said pellets to metallic copper. The reduction step is normally carried out in the reactor where the carbon oxide conversion process is to be effected: thus normally a catalyst precursor in which the copper is present in the form of copper oxide is charged to the reactor and the reduction effected by passing a suitable gas mixture there-through. The reduction of copper oxide is exothermic and the in-situ reduction step is often carried out over extended periods using dilute hydrogen streams to avoid damaging the catalyst. Such extended start-up procedures are difficult to control and can be costly to operate.

By such precipitation/calcination/reduction techniques, the catalysts generally have a copper surface area above 20 $m^2$ per gram of copper, often above 40 $m^2$ per gram of copper. Commercially available carbon oxide conversion catalysts typically have a copper surface area about 50 $m^2/g$ per gram of copper. Copper surface area may be measured by the nitrous oxide decomposition method, e.g. as described in the article by Evans et al. in *Applied Catalysis* 1983, 7, 75-83 and a particularly suitable technique is described in EP 0202824.

Since the activity of the catalysts is linked to the copper surface area, it is desirable to obtain catalysts with higher copper surface areas.

U.S. Pat. No. 4,863,894 describes a process for the manufacture of a catalyst comprising forming a composition comprising an intimate mixture of discrete particles of compounds of copper, and zinc and/or magnesium and, optionally, at least one element X selected from aluminium, vanadium, chromium, titanium, zirconium, thorium, uranium, molybdenum, tungsten, manganese, silicon, and the rare earths, and subjecting the composition to reduction conditions so that the copper compounds therein are converted to copper, wherein the copper compounds in the intimate mixture are reduced to metallic copper without heating said intimate mixture to a temperature above 250 DEG C. The direct reduction of the precipitated catalyst precursor compositions, rendered catalysts having copper surface areas >70 $m^2$ per gram copper.

However copper surface area is not the only criterion that needs to be taken into account for carbon oxides conversion catalysts. In particular catalyst strength and stability, both in terms of activity and selectivity, are also important. Mean Horizontal Crush Strength (MHCS) is a method widely used in the catalyst industry to measure the strength of catalyst pellets. MHCS is routinely measured on pellets to ensure their strength is sufficient to undergo the stresses applied during catalyst loading and to give an indication of strength in duty. The catalysts obtained by the process of U.S. Pat. No. 4,863,894 do not have the high strength stability required in modern carbon oxides conversion processes, and currently oxidic catalysts are still used.

We have now devised catalysts of increased copper surface area that overcomes the disadvantages of the previous catalysts.

SUMMARY OF THE INVENTION

Accordingly the invention provides a carbon oxides conversion process which comprises reacting a carbon oxide containing process gas containing hydrogen and/or steam and containing at least one of hydrogen and carbon monoxide in the presence of a catalyst comprising shaped units formed from a reduced and passivated catalyst powder said powder comprising copper in the range 10-80% by weight, zinc oxide in the range 20-90% by weight, alumina in the range 5-60% by weight, and optionally one or more oxidic promoter compounds selected from compounds of Mg, Cr, Mn, V, Ti, Zr, Ta, Mo, W, Si and rare earths in the range 0.01-10% by weight, wherein said shaped units have a re-reduced to as-made mean horizontal crush strength ratio of 0.5 and a copper surface area above 60 $m^2/g$ Cu.

The invention further provides a catalyst suitable for use in carbon oxide conversion reactions in the form of a shaped unit formed from a reduced and passivated catalyst powder said powder comprising copper in the range 10-80% by weight, zinc oxide in the range 20-90% by weight, alumina in the range 5-60% by weight, and optionally one or more oxidic promoter compounds selected from compounds of Mg, Cr, Mn, V, Ti, Zr, Ta, Mo, W, Si and rare earths in the range 0.01-10% by weight, wherein said shaped units have a re-reduced to as-made mean horizontal crush strength ratio of 0.5 and a copper surface area above 60 $m^2/g$ Cu.

The invention further provides a method for making the catalyst comprising the steps of:
(i) forming, in an aqueous medium, a composition comprising an intimate mixture of discrete particles of compounds of copper, zinc, aluminium and optionally one or more compounds selected from compounds of Mg, Cr, Mn, V, Ti, Zr, Ta, Mo, W, Si and rare earths, (ii) recovering and drying the composition to form a catalyst precursor, (iii) subjecting the dried catalyst precursor composition to reduction conditions so that the copper compounds therein are converted to copper, (iv) passivating the reduced copper surfaces, and (v) shaping the reduced and passivated composition, characterised in that, prior to the reduction of the copper compounds, the intimate mixture is subjected to a drying step at a temperature in the range 180-240° C.

The drying step, which does not convert the copper compounds to copper oxide, provides a catalyst precursor capable of giving shaped units with a high strength that retains the potential for a high copper surface areas upon reduction. The passivation step produces a protective layer on the surface of the reduced copper and allows for the safe shaping of the reduced composition. In the present invention, bulk conversion of the copper compounds to copper oxide, e.g. by calcining the composition, is highly undesirable as this leads to catalysts with lower copper surface areas, and hence lower activity.

DETAILED DESCRIPTION OF THE INVENTION

The catalyst of the present invention is particularly useful because it offers faster start-up than conventional oxidic catalysts, offers higher activity though its higher copper surface area, which in turn offers the potential for smaller reactors and/or higher productivity, and gives a high strength pellet which has a number of advantages including the production of new shapes that offer reduced pressure drop in the conversion processes.

The copper content (expressed as Cu atoms) of the active catalyst is typically in the range 10-80%, preferably 15-70%, by weight. Within this range a copper content in the range 50-70% by weight is of general application for methanol synthesis, whereas for the shift reaction the copper content is generally somewhat lower, particularly in the range 15-50% by weight. In the catalyst of the present invention the copper will be present in an oxidised form in the passivation layer and in elemental form beneath this layer. Preferably in the catalyst as made <50% (by atoms) more preferably <40% (by atoms) of the copper is in oxidised form.

In addition to metallic copper, the catalyst can contain one or more other metals having catalytic activity: where the process is alcohol synthesis, examples of such other metals are cobalt, palladium, rhodium, or ruthenium. Optionally metallic silver can be present. Other catalytically active metals, if present, are normally present in relatively low proportions; the proportion of such other catalytically active metals is typically 1-10 atoms of such metals per 100 atoms of copper.

Copper containing catalysts suffer from a problem that, upon heating above about 250° C., the copper atoms tend to sinter together giving a decrease in the copper surface area after a period of use at elevated temperature with consequent loss of activity. In order to alleviate this disadvantage, the catalyst contains at least one further material, including zinc compounds and optionally one or more promoter compounds selected from compounds of Mg, Cr, Mn, V, Ti, Zr, Ta, Mo, W, Si and rare earths. In the catalyst, the zinc oxide content may be in the range 20-90% by weight, and the one or more oxidic promoter compounds, if present, may be present in an amount in the range 0.01-10% by weight. Magnesium compounds are preferred and the catalyst preferably contains magnesium in an amount 1-5% by weight, expressed as MgO. The promoter compounds are not reduced to metal under the process conditions and are typically present as one or more oxides in the catalyst.

Aluminium in the form of aluminium oxide, which may be a partially hydrated aluminium oxide, is also present in the catalyst. The amount of aluminium oxide may be in the range 5-60% by weight (expressed as $Al_2O_3$). The aluminium oxide may be included directly or formed from aluminium compounds that decompose to the oxide or hydrated oxide.

A preferred catalyst precursor composition comprises, prior to reduction, a solid containing mixed metal carbonates, including hydroxycarbonates, of Cu and Zn, with alumina or hydrated alumina dispersed therein and optionally containing one or more Mg, Cr, Mn, V, Ti, Zr, Ta, Mo, W, Si or rare earths compounds, particularly Mg compounds, as a promoter. The catalyst preferably contains 30-70% wt copper (expressed as CuO). The weight ratio of Cu:Zn (expressed as CuO:ZnO) may be 1:1 or higher but is preferably is in the range 2:1 to 3.5:1 by weight for alcohol synthesis catalysts and in the range 1.4:1 to 2.0:1 for water-gas shift catalysts.

Particularly preferred catalyst compositions suitable for methanol synthesis have molar ratios of Cu:Zn:Mg:Al in the ranges 16.5 to 19.5:5.5 to 8.5:1.0:2.5 to 6.5. Particularly preferred catalyst compositions suitable for water-gas shift reaction have molar ratios of Cu:Zn:Mg:Al in the ranges 10 to 15:6 to 10:1:6 to 12.

As mentioned above, copper-containing catalysts are conventionally prepared by forming an intimate mixture of particles of compounds of copper, and zinc, calcining the mixture, often in an oxygen-containing atmosphere, usually air, to convert those compounds to oxides, followed by pelleting, and then reduction. The calcination is normally effected at temperatures in an excess of 275° C. and is generally effected at temperatures in the range 300 to 500° C.

In the present invention, in order to obtain the high copper surface areas, the calcination step is omitted, and the intimate mixture is subjected to reduction conditions so that the copper compounds therein are converted to copper without an initial discrete step of heating to convert the copper compounds to copper oxide. Rather, the drying is carefully controlled to ensure that the water is driven off as completely as is possible without causing the decomposition of the copper compounds to copper oxide.

The copper surface areas of the catalysts obtainable in the present invention are 60 $m^2$/g Cu, preferably ≥70 $m^2$/g Cu, more preferably 75 $m^2$/g Cu, most preferably 80 $m^2$/g Cu. As stated above the copper surface area may be readily established by using reactive frontal chromatography as described in EP-A-202824. A particularly suitable method is as follows; Catalyst shaped units are crushed and sieved to particle size of 0.6-1.00 mm. About 2.0 g of the crushed material is weighed into in a glass tube and heated to 30° C. (for reduced and passivated samples) or 68° C. (for oxidic samples) and purged with helium for 2 minutes. Then the catalyst is reduced by heating it in a flow of 5% vol $H_2$ in helium, at 4° C./min up to 230° C. and then holding it at this temperature for 30 minutes. Catalyst is then cooled to 68° C. under Helium. The reduced catalyst then has 2.5% vol $N_2O$ in helium passed over the catalyst. The evolved gases are passed through a gas chromatograph and the $N_2$ evolution is measured. From this the copper surface area of the catalyst may be calculated.

The crush strength ratio of the catalyst shaped units of the present invention, is the ratio of the mean horizontal crush strength (in kilograms) of the reduced shaped unit to the mean horizontal crush strength (in kilograms) of the catalyst shaped unit as made. In the catalyst of the present invention this ratio is ≥0.500:1, preferably ≥0.600:1, more preferably ≥0.650:1, most preferably ≥0.700:1, especially ≥0.750:1. Measurement of the ratio requires a measurement of the crush strength of the catalyst shaped units as made, i.e. the shaped units formed from the reduced and passivated powder, and also on the re-reduced shaped unit, i.e. of the shaped units once the copper passivation layer has been re-converted to elemental copper by exposure to a reducing gas stream. Hence, the strength of the catalyst shaped units as made may be performed on the reduced and passivated catalyst in air whereas the strength of the re-reduced catalyst is desirably measured under an inert atmosphere to prevent exothermic oxidation of the shaped unit. The crush strength of the catalyst as-made, expressed as the mean horizontal crush strength, is preferably ≥6.5 kg more preferably ≥10.0 kg most preferably ≥12.0 kg so that the catalyst has sufficient strength to be loaded into the reactor for the carbon oxides conversion process. The mean horizontal crush strengths (MHCS) may be determined using conventional techniques. A suitable method for the as-made shaped units is as follows. Crush strength of the shaped units are measured on cylindrical pellets of diameter in the range 5-6 mm using a calibrated CT5 pellet strength testing machine. Pellet crush strengths are measured in the horizontal (i.e. radial) plane. A 50 kg load cell is used and the crush strength speed is 2.5 mm/min. At least 20 pellets are tested and the average figure quoted. For measuring the crush strengths on reduced pellets, the oxidic or reduced and passivated pellets must first be subjected to a reduction step. This may be achieved by placing the pellets in a vessel, purging the air with nitrogen and then exposing the pellets to 2% $H_2$ in nitrogen and heating to 90° C. over 2 hours, then to 120° C. over a further 2 hours, then to 180° C. over a further 5 hours and then 235° C. over a further 7 hours, holding at 235° C. for 3 hours, then heating to 240° C. over a further 1 hour and then holding at 240° C. for 3 hours before cooling in the presence of the reducing gas and purging with nitrogen for storage. The reduced pellets are and tested under an inert (i.e. $O_2$-free) atmosphere using the CT 5 equipment located in a glove-box.

Since there is no calcination step prior to reduction, the intimate mixture is not shaped prior to reduction because the intra-pellet voidage resulting from the decomposition of e.g. hydroxycarbonate compounds, during which water and/or carbon dioxide is evolved, can result in low mechanical strength and thus short process life.

The intimate mixture can be made by wet treatment of oxides, such as by reacting copper oxide, zinc oxide, and ammonia together in an aqueous medium such as water, or by mixing soluble metal compounds. More conveniently, it is made by decomposition of metal nitrates with an alkaline precipitant in an aqueous medium such as water, for example as described in GB-A-1010871, GB-A-1159035, GB-A-1296212 and GB-A-1405012. The reaction and after-treatment conditions of the resulting slurry can be chosen to produce definite crystalline compounds for example of the Manasseite, Rosasite, Aurichalcite or Malachite type. A suitable procedure comprises co-precipitating soluble salts of the metals with a precipitant such as an ammonium, or alkali metal, hydroxide, carbonate or bicarbonate. The order in which the reactants are mixed may be optimised following known principles, for example employing single-stage co-precipitation as in GB-A-1159035 or 2-stage co-precipitation as in GB-A-1296212 and GB-A-1405012. Preferably all the divalent oxide constituents are introduced by such co-precipitation.

In a preferred embodiment, insoluble copper compounds and one or more other insoluble metal compounds are precipitated by combining an aqueous solution of one or more soluble metal compounds, such as a metal nitrate, sulphate, acetate, chloride or the like, and an aqueous solution of an alkaline carbonate precipitant, such as sodium or potassium carbonate. Non-carbonate precipitants may also be present such as alkali metal hydroxides or ammonium hydroxide. Hence, the intimate mixture of discrete particles may be formed by combining aqueous solutions of soluble metal compounds of copper, zinc and optionally one or more promoter metal compounds selected from compounds of Mg, Cr, Mn, V, Ti, Zr, Ta, Mo, W, Si or rare earths, with an aqueous solution of an alkaline carbonate precipitant in the presence of an alumina or hydrated alumina, or an aluminium compound decomposable thereto. In a preferred embodiment, a colloidally-dispersed aluminium oxide or aluminium hydroxide is used as the source of alumina. Such colloidally-dispersed aluminium oxides or aluminium hydroxides are commercially available or may be prepared using known methods. Their use in preparing copper catalysts is described, for example, in U.S. Pat. No. 4,535,071. Upon combining the metal solution and precipitant solution, the alkaline carbonate reacts with the soluble metal compound forming an insoluble metal carbonate, including metal hydroxy-carbonate. Ageing of the precipitated material may be carried out in a batch or semi-continuous procedure whereby the aqueous slurry of the precipitated material held at elevated temperatures in one or more stirred vessels for selected periods of time. Suspension of the compounds in the liquid can be by mere stirring, the vigour of stirring depending on the tendency of the particles to settle. If desired, a polymer can be present in solution to inhibit settling. Alternatively the precipitated material may be aged in a pulse-flow reactor as described in our WO2008/047166, which is herein incorporated by reference.

After such mixing, the intimate mixture is desirably recovered, e.g. by separation of the mother liquors using known methods such as filtering, decanting or centrifuging, and washed to remove soluble salts. Especially when alkali metal compounds are present, the alkali content should desirably be reduced to below 0.2% wt, preferably below 0.1% wt, more preferably below 0.05% wt calculated as the respective alkali metal oxide on the dried material.

After any washing, the material is dried to form a catalyst precursor powder in a process including a stage performed at a maximum temperature in the range 180-240° C. The drying may therefore comprise heating the damp mixture in discrete stages or continuously over an extended period until the maximum temperature is reached. Preferably the drying step is performed using two or more distinct drying steps that remove the water in stages. The drying step may be performed using conventional drying equipment, such as that used for the oxidic catalysts. In one embodiment drying comprises an initial step of heating the damp intimate mixture to a temperature in the range 90-150° C., preferably 100-125° C. under air or an inert gas in an oven, rotary drier or similar equipment prior to drying at 180-240° C. In an alternative embodiment, the initial drying step is performed using a spray-drier, which also acts to generate agglomerates of the intimate mixture particularly suitable for compression shaping into pellets. To facilitate spray drying, the washed material is desirably dispersed in water. The solids content of the spray drier feed may be above 15% by weight but is preferably ≥20% by weight. Conventional sprayer equipment may be used with an inlet temperature in the range 150-300° C., and an out let temperature in the range 100-200° C. In circumstances where the inlet temperature is above 240° C., the feed rate should be controlled so that the copper compounds suffer substantially no thermal decomposition. Spray-dried agglomerates with an average particle size (as determined by sieve fractions, i.e. the weight-average particle size) in the range 10-300 μm (microns) are preferred, particularly 100-250 μm.

Initial drying, whether by oven or spray drying, desirably reduces the water content of the catalyst precursor to <20% wt, preferably <15% wt, more preferably ≤10% wt.

Whether subjected to a one-step drying process or a discrete number of drying steps, the intimate mixture is subjected to a drying step in which it is heated to a temperature in the range 180-240° C. Without wishing to be bound by theory, it is believed that drying at these temperatures removes the chemisorbed as well as physisorbed water from the catalyst precursor and that this renders a catalyst precursor with increased strength. The time it is held at the temperature in this range depends on the temperature chosen, with more extended periods desirable for lower temperatures in the range and shorter periods for higher temperatures. A maximum drying temperature of 210-240° C. is therefore preferred. Drying times in the range 2 to 8, preferably 2 to 6 hours are desirable. The drying step may be performed in air or an inert gas, such as nitrogen or argon in an oven, rotary drier or other conventional drying equipment. As stated above, the drying step does not convert the copper compounds, e.g. copper hydroxycarbonate compounds, to copper oxide. After drying, the catalyst precursor is desirably stored under de-humidified air or dry inert gas to prevent re-adsorption of atmospheric water.

Reduction of the copper compounds may conveniently be achieved by exposing the dried catalyst precursor to a hydrogen- and/or carbon monoxide-containing gas at atmospheric or elevated pressure. Reduction is carried out preferably at the lowest temperature at which it will proceed. Thus conventional hydrogen reduction techniques may be used wherein a dilute hydrogen stream, e.g. 2% $H_2$ in $N_2$ is used and the catalyst precursor heated slowly until reduction commences. Generally it is found that reduction begins at about 80° C. and is sufficiently complete by 200° C. or even 150° C.

In the present invention, we have observed that reduction of catalyst precursors containing copper carbonate compounds, such as copper hydroxycarbonate (malachite) and/or zincian malachite, may be performed with high concentrations of hydrogen in the reducing gas stream for the entire reduction stage without the problems normally observed in the reduction of copper-oxide containing materials. In a preferred embodiment therefore, reduction of catalyst precursors containing copper hydroxycarbonate materials is performed by exposing the dried catalyst precursor to hydrogen-containing gas streams comprising >50% vol hydrogen, more preferably >75% vol hydrogen, especially >90% vol hydrogen. If desired, substantially pure hydrogen may even be used.

The reduction may be monitored using conventional techniques. For example, the reduction may be performed on copper hydroxy-carbonate containing catalyst precursors until no further water and carbon dioxide are evolved. The reduction normally converts at least 50% of the reducible compounds, e.g. copper carbonates, to metal but is preferably continued until >95% of the reducible compounds are converted to metal. The zinc and promoter compounds are largely converted to their respective oxides during the reduction stage.

In a particularly preferred method, the reduction is performed by fluidising the powdered precursor in the reducing gas stream, in a suitable vessel. The vessel may be externally cooled and/or the reducing gas may be subject to heat exchange to both control the temperature of the reducing material and also condense and remove water from the reducing gas. The dried reducing gas is desirably re-circulated to the fluidised material. This method offers a particularly convenient method to rapidly reduce the catalyst precursor in the fastest time.

In the reduced state, because of the high surface area, the copper may rapidly and exothermically react with oxygen and moisture present in the air and so it has to be passivated for shaping and storage. The composition is considered passivated when it is stable to air, particularly air at temperatures >50° C. This may determined by thermogravimetric analysis (TGA) in which the weight change of the material is monitored as it is heated. As oxidation occurs, the catalyst increases in weight. Desirably, the passivated catalyst shows no substantial weight gain when heated in air at 20° C./min until the temperature has reached at least 80° C., preferably at least 90° C.

Passivation may be performed using dilute oxygen and/or carbon dioxide or the catalyst precursor powder may be coated with an oxygen barrier material. Passivation may be achieved by using inert gas/air mixtures, such as nitrogen/air mixtures, whereby the air concentration is slowly increased over a period in order to generate a thin metal oxide layer on the copper surfaces. Typically oxygen is introduced using air at a rate sufficient to maintain the temperature of the catalyst precursor at between 10 and 100° C., preferably 10 and 50° C., especially 20-40° C. during the passivation. For example the reduced material may be exposed to an inert gas, e.g. nitrogen, flow and air added at 0.1% vol. This is carefully increased over a period of time to 0.5% vol oxygen, then 1% vol, then 2% vol, 5% vol and so on until the oxygen content is that of air. Alternatively, reduced catalyst compositions may be passivated using a gas mixture comprising carbon dioxide and oxygen with a $CO_2:O_2$ ratio ≥2:1 in order to form a thin layer of a metal carbonate, e.g. a metal hydroxy-carbonate, on the surface.

In a preferred method, the passivation is performed by fluidising the powdered reduced precursor in an inert gas such as nitrogen and then feeding oxygen and/or carbon dioxide containing gases, such as air or a mixture of air and carbon dioxide in at low concentrations. The vessel may be externally cooled and/or the passivating gas may be subject to heat exchange to control the temperature of the passivating material.

If desired, the fluidisation vessel may used for both the reduction and passivation stages as this removes the risk of exposing the reduced precursor to oxygen during storage.

The reduced and passivated catalyst precursor powder can then be further processed to give shaped units, inter alia the following steps being possible:
(i) Pre-compaction and pelleting of the reduced and passivated powder, such that the shaped units are pellets,
(ii) Combination of the reduced and passivated powder with one or more binders, and optionally one or more further powder materials and tumbling to form spherical agglomerates or granules,
(iii) Conversion of the reduced and passivated powder into a slurry (preferably non-aqueous), kneading/grinding in a pan mill and extrusion to form extrudates.
(iv) Conversion into a slurry as above, kneading/grinding in a pan mill and extrusion to give complex mouldings, such as monolithic structures or catalyst plates with or without secondary structure.
(v) Application of the reduced and passivated powder to inert or likewise catalytically active supports by means of wash-coating or similar processes.

In all processes, the use of binders and additives common in the art may be used. Numerous other possibilities for further processing are also possible.

Pre-compaction and pelleting of the powder is most suitable for preparing shaped units of the present invention. The pellet may be the conventional flat-ended cylindrical pellet. Cylindrical pellets for carbon oxide conversion processes suitably have a diameter in the range 2.5-10 mm, preferably 3-10 mm and an aspect ratio (length/diameter) in the range 0.5-2.0. Alternatively, the shaped unit of the present invention may be in the form of rings or trilobes. In a preferred embodiment the shaped unit is in the form of a domed cylinder having two or more grooves running along its length. In one such embodiment, the catalyst is in the form of a cylinder having a length C and diameter D, wherein the exterior surface of the unit has two or more flutes running along its length, said cylinder having domed ends of lengths A and B such that (A+B+C)/D is in the range 0.50 to 2.00, and (A+B)/C is in the range 0.40 to 5.00. A and B are preferably the same. C is preferably in the range 1 to 25 mm, D is preferably in the range 4 to 40 mm, more preferably 4 to 10 mm, and most preferably there are 4-flutes evenly spaced around the cylinder. Alternatively, or in addition, the shaped units may have one or more through-holes extending there-through. Such highly domed cylindrical catalysts have improved packing and/or lower pressure drop than conventional non-fluted or non-holed shapes. Such adaptation of the conventional flat-ended cylindrical catalyst shape has been made possible by the improved strength properties of the reduced and passivated catalyst precursor powder.

Pellets, particularly cylindrical pellets with flat or domed ends as described above, are desirably made with pellet densities in the range 1.4 to 2.5 g/cm$^3$, more preferably 1.8 to 2.4 g/cm$^3$. The pellet density may readily be determined by calculating the volume from the pellet dimensions and measuring its weight. As the density is increased, the interstitial volume in the shaped units is reduced, which in turn reduces the permeability of reacting gases into and out of the unit. Therefore for densities >2.5 g/cm$^3$ the reactivity of the catalyst may be less than optimal, despite the high copper surface area of the reduced and passivated powder. For densities <1.4 g/cm$^3$ the crush strengths may be insufficient for long-term use in modern carbon-monoxide conversion processes.

The BET surface area of the reduced and passivated catalyst, as determined by nitrogen absorption is desirably >80 m$^2$/g, more desirably >90 m$^2$/g; and the pore volume, as determined using the desorption branch at 0.99, is desirably >0.15 cm$^3$/g, more desirably >0.2 cm$^3$/g.

The invention includes a carbon oxides conversion process, which comprises reacting a carbon oxide containing process gas containing hydrogen and/or steam and containing at least one of hydrogen and carbon monoxide in the presence of the catalyst. The catalyst may be pre-activated in-situ by exposing it to a reducing gas stream, preferably comprising hydrogen to convert the passivated copper layer back into elemental copper. Thus the invention preferably includes the steps of (i) activating the catalyst by contacting said catalyst with a reducing gas stream and (ii) reacting a carbon oxide containing process gas containing hydrogen and/or steam and containing at least one of hydrogen and carbon monoxide in the presence of a catalyst to form a product stream. Because the bulk of the copper is already in metallic form, this activation step may be performed more quickly and with less water-by-product to be removed than with conventional copper oxide-containing catalysts. Activation may be performed using a hydrogen containing gas, including synthesis gas comprising hydrogen and carbon oxides, at temperatures above 80° C. and at pressures in the range 1-50 bar g. Again the maximum reduction temperature is desirably 150 to 200° C.

The invention provides processes using the catalyst, in particular:

A. Methanol synthesis in which a gas mixture containing carbon monoxide, hydrogen and optionally carbon dioxide, is passed over the catalyst at a temperature in the range 200-320° C., a pressure in the range 20-250, especially 30-120, bar abs and a space velocity in the range 500-20000 h$^{-1}$. The process can be on a once-through, or a recycle, basis and can involve cooling by indirect heat exchange surfaces in contact with the reacting gas, or by subdividing the catalyst bed and cooling the gas between the beds by injection of cooler gas or by indirect heat exchange. For this process the catalyst preferably contains copper, zinc oxide and magnesia, with alumina.

B. Modified methanol synthesis in which the catalyst contains also free alumina of surface area 50-300 m$^2$ g$^{-1}$, so that the synthesis product is relatively rich in dimethyl ether. Temperatures, pressures and space velocities are similar to those for methanol synthesis but the synthesis gas contains hydrogen and carbon monoxide in a molar ratio of less than 2.

C. Modified methanol synthesis in which the catalyst contains also alkali at a level in the range 0.2 to 0.7% by weight, particularly potassium, added in a discrete step to the intimate mixture, so that the synthesis product contains higher alcohols (containing 2 to 5 carbon atoms), usually in addition to methanol. Process conditions are generally similar to those for B, but higher pressures and temperatures and lower space velocities in the stated ranges are preferred.

D. Low temperature shift reaction in which a gas containing carbon monoxide (preferably under 4% v/v on a dry basis) and steam (steam to total dry gas molar ratio typically in range 0.3 to 1.5) is passed over the catalyst in an adiabatic fixed bed at an outlet temperature in the range 200 to 300° C. at a pressure in the range 15-50 bar abs. Usually the inlet gas is the product of "high temperature shift" in which the carbon monoxide content has been decreased by reaction over an iron-chromia catalyst at an outlet temperature in the range 400 to 500° C., followed by cooling by indirect heat exchange. The outlet carbon monoxide content is typically in the range 0.1 to 1.0%, especially under 0.5% v/v on a dry basis.

E. Medium temperature shift in which the gas containing carbon monoxide and steam is fed at a pressure in the range 15-50 bar abs to the catalyst at an inlet temperature typically in the range 200 to 240° C. although the inlet temperature may be as high as 280° C., and the outlet temperature is typically up to 300° C. but may be as high as 360° C. These conditions are more severe than in D, such that the new catalyst is expected to be especially advantageous.

F. Low-medium temperature shift with heat exchange, in which the reaction in the catalyst bed occurs in contact with heat exchange surfaces. The coolant conveniently is water under such a pressure such that partial, or complete, boiling takes place. A suitable pressure is 15 to 50 bar abs and the resulting steam can be used, for example, to drive a turbine or to provide process steam for shift, or for an upstream stage in which the shift feed gas is generated. The water can be in tubes surrounded by catalyst or vice versa. Two particular modes of operating this type of shift process are envisaged:

(i) Falling temperature profile, for example 240 to 350° C. inlet range and (especially 240 to 310° C.) with typically a fall of up to 50° C. (especially 10 to 30° C.) between inlet and outlet. This permits better heat recovery upstream because a feed gas produced at high temperature can be cooled to a temperature lower than in the conventional process. It also permits an outlet carbon monoxide content as low as in conventional low temperature shift;

(ii) Rising temperature profile, for example at an inlet temperature in the range 100 to 240° C. rising to a maximum of 240 to 350° C., followed by a falling temperature profile as in (i) above. This is suitable for shifting a gas made by partial oxidation of coal, or heavy hydrocarbon feedstocks, followed by treatments at ambient temperature, or below, to remove carbon, dust and sulphur compounds. The hot water in heat exchange brings the feed gas up to the temperature at which the shift reaction proceeds rapidly. In such a process, the inlet zone in the shift catalyst bed may be a preheat zone charged with inert granules such as alpha alumina. In any such shift processes it may be desirable to protect the catalyst from poisoning, such as by sulphur or chlorine compounds, and for this purpose a guard bed of expendable catalyst or zinc oxide or alkalised alumina can be disposed upstream.

Processes involving heat exchange are described further in EP-A-157480. The provision of the heat exchange also assists in controlling catalyst temperature during reductive activation and also, by coping with any fall in temperature below the dew point of steam, makes it practicable to use a chloride guard, such as alkalised alumina, in an inlet zone above the catalyst.

Alternatively for alcohol synthesis reactions, instead of using a fixed bed catalyst, the catalyst may be suspended in a liquid. While in principle the particles obtained by the aforementioned techniques for obtaining a catalyst suitable for use in a fixed bed could also be used in suspension in a liquid, it is preferred to use the labile compounds as powder or in some small particle form agglomerated to an extent short of what is needed in a fixed bed process.

EXAMPLES

The invention will now be further described by reference to the following Examples.

Copper surface area and mean horizontal crush strength were measured using the methods described above. Crush strengths were measured using a CT5 desktop automatic mechanical strength tester (manufactured by Engineering Systems (Nottn) Ltd).

X-Ray Diffractommetry (XRD) was carried out using a Bruker AXS D8 advance diffractometer in parallel beam mode using nickel-filtered Cu Kα radiation and $LaB_6$ as a line profile standard.

Pellet shrinkage was measured by hand using digital callipers. Pellets before and after reduction were physically measured for volume changes. The reduced pellets were examined in a glove-box under an inert (i.e. $O_2$-free) atmosphere. 20-50 pellets were examined and an average is quoted.

Example 1

Catalyst Preparation

A catalyst precursor powder was prepared with the molar ratio Cu:Zn:Mg:Al of 17.5:6.5:1:4 by precipitating at 60-75° C. and a pH above 6.0, an intimate mixture from solutions of copper, zinc and magnesium nitrates in the presence of a colloidally-dispersed aluminium hydroxide sol, using potassium carbonate as precipitant. Once the co-precipitation had been completed the slurry was aged at 65° C. until the colour transition from blue to green occurred. The slurry was then filtered and washed until the alkali levels were at a minimum level (<500 ppm).

The resultant filter cake was then re-slurried to achieve a 35% w/w slurry and then spray-dried to form agglomerates of about 10-50 μm in diameter.

The spray-dried powder was then subjected to a drying step by heating it to 210-240° C. and maintaining it at this temperature for 6 hours. XRD analysis confirmed the presence of copper hydroxycarbonate and showed no formation of copper oxide during the drying step. The catalyst precursor material was then cooled to 60-80° C. in dry nitrogen.

The catalyst precursor was reduced by exposing it to a hydrogen-containing gas comprising >90% $H_2$, initially at about 80° C. with reduction performed at a maximum temperature of 160° C. The reduction process was continued until water and carbon dioxide were no longer evolved as measured using conventional detectors. Calculations indicated >95% of the copper was converted to elemental form. The reduced catalyst material was then cooled to 20-40° C. under dry nitrogen.

The reduced catalyst material was then passivated at 20-40° C. using nitrogen/air mixtures controlled initially to provide 0.1% vol oxygen and then increased gradually to 1% vol oxygen and then higher amounts until the passivating gas was 100% air. The rate of increasing the oxygen content was controlled by monitoring the temperature.

The passivated catalyst powder was mixed with a little graphite and shaped into cylindrical pellets using conventional pelleting equipment in air. The pellets were 5.4 mm diameter by 3.2 mm in length.

In comparison, a comparative catalysts having the same Cu:Zn:Mg:Al molar ratio, were prepared by the same precipitation process and spray dried using the same spray-drying method but instead of a high-temperature drying step, the spray-dried powders were subjected to a calcination at (I) 295° C. or (II) 500° C. wherein the copper compounds were converted to copper oxide. The resulting oxidic powders were again mixed with a little graphite and shaped into cylindrical pellets of 5.4 mm diameter by 3.2 mm length.

The copper surface areas of the pellets were determined by reactive frontal chromatography as described above. In each case the surface areas were measured on crushed and sieved pellets. The results were as follows;

| Sample | Copper surface area $m^2/g$ Cu |
|---|---|
| Comparative material I (calcined 295° C.) | 40.0 |
| Comparative material II (calcined 500° C.) | 38.8 |
| Example 1 | 89.6 |

The results show that the copper surface areas of the reduced and passivated catalyst in accordance with the present invention are superior to those wherein the preparation includes a calcination step.

The MHCS was determined on the pellets as made and also following a reduction to simulate the strength in-situ.

| Pelleted material | Pellet Density g/cm³ | MHCS pellets as made (kg) | MHCS Reduced pellets (kg) | MHCS Ratio (Reduced:as made) |
|---|---|---|---|---|
| Comparative Catalyst I | 1.97 | 12.2 | 2.4 | 0.197:1 |
| Comparative Catalyst II | 1.97 | 8.4 | 2.6 | 0.310:1 |
| Example 1a | 2.04 | 17.2 | 14.3 | 0.831:1 |

The results show that very high crush strengths maybe achieved and that at comparable density, the pellets made from a precursor powder made with a calcination step are surprisingly weaker post-reduction than those of the present invention.

Example 2

The catalyst preparation of Example 1 was repeated using sodium carbonate as precipitant in place of the potassium carbonate.

The spray drier feed had a solids content of 37% wt.
Spray Drier settings were:
Inlet Temperature: 350° C.
Outlet temperature: 110° C.
Pump Pressure: 40 bar Residual moisture content of the powder after spray drying was 4.7%, but the particles were free flowing. 92% wt of the particles had a particle size 53-250 μm (microns) with 62.3% wt of the particles having a particle size in the range 100-180 μm.

The spray-dried product was subjected to the same drying step, reduction and passivation as Example 1. The reduced and passivated powder was again shaped into cylindrical pellets of diameter 5.4 mm and length 3.2 mm, with a pellet density of about 2.0. The copper surface area was measured on these pellets using the above method.

| Sample | Copper surface area m²/g Cu |
|---|---|
| Example 2 | 83.0 |

A range of pellet densities was also explored. The MHCS was determined on the pellets as made and also following a re-reduction to simulate the strength in-situ. The results were as follows:

| Sample | Pellet Density g/cm³ | MHCS as made kg | MHCS Re-Reduced kg | MHCS Ratio |
|---|---|---|---|---|
| Example 2a | 1.73 | 7.5 | 6.5 | 0.867:1 |
| Example 2b | 1.76 | 8.0 | 6.6 | 0.825:1 |
| Example 2c | 2.00 | 15.9 | 13.5 | 0.849:1 |
| Example 2d | 2.06 | 18.2 | 14.9 | 0.819:1 |
| Example 2e | 2.25 | 23.4 | 16.3 | 0.697:1 |

In comparison, a conventional oxidic copper-catalyst having the same Cu:Zn:Mg:Al molar ratio and prepared using the same sodium precipitant gave a MHCS upon reduction of the oxidic pellets of about 2.5 kg (at a pellet density of 1.97).

Example 3

The catalyst preparation of Example 1 was repeated.
The spray drier feed had a solids content of 20-25% wt.
Spray Drier settings were:
Inlet Temperature: 290-300° C.
Outlet temperature: 114-120° C.
Pump Pressure: 18-20 bar Residual moisture content of the spray-dried powder was 8-10%. 95% wt of the particles had a particle size 63-250 μm (microns) with 62.8% wt of the particles having a particle size in the range 150-210 μm.

The spray-dried product was subjected to the same drying step, reduction and passivation as Example 1. Again the reduced and passivated powder was formed into cylindrical pellets with diameter 5.4 mm and length 3.2 mm and a pellet density of about 2.0.

The copper surface area was measured using the above method.

| Sample | Copper surface area m²/g Cu |
|---|---|
| Example 3 | 80.1 |

A range of pellet densities was also explored. The MHCS was determined on the pellets as made and also following a re-reduction to simulate the strength in-situ. The results were as follows.

| Sample | Pellet Density (g/mL) | MHCS As-Made (kg) | MHCS Re-reduced (kg) | MHCS Ratio | Shrinkage on Reduction (% v/v) |
|---|---|---|---|---|---|
| Example 3a | 1.73 | 8.8 | 6.9 | 0.784:1 | 11.2 |
| Example 3b | 1.94 | 14.6 | 10.3 | 0.705:1 | 9.9 |
| Example 3c | 2.10 | 17.7 | 10.7 | 0.604:1 | 10.1 |

The properties of the as-made pellets (crushed and sieved) were measured using nitrogen absorption as follows:

| Sample | BET SA (m²/g) | Pore Volume (cm³g⁻¹) |
|---|---|---|
| Example 3a | 95.7 | 0.30 |
| Example 3b | 94.0 | 0.27 |
| Example 3c | 91.5 | 0.24 |

Example 4

Testing-Methanol Synthesis

A sample of the pellets from Examples 1 to 3 was crushed and 2 ml (0.50 g) of fragments in the sieve range 0.6-1.0 mm were charged to a micro-reactor and reduced to active catalyst in a 2% vol $H_2/N_2$ gas mixture up to 240° C. A methanol synthesis gas of % v/v composition 6.0 CO, 9.2 $CO_2$, 67.0 $H_2$, and 17.8 $N_2$ was passed over the catalyst at a pressure of 50 barg, temperature 225° C. and space velocity 40000 $h^{-1}$. The outlet methanol was measured on-line using a combination of infrared and gas chromatography systems. Then, for an accelerated life test, the pressure and temperature were raised to above normal operating conditions; these conditions were held to 144 h, then decreased to their former levels, at which the outlet methanol content was measured again.

The relative activities of the catalysts of Examples 1a, 2c and 3b, each having a pellet density about 2.0, are given below. The activity quoted is relative to that of a standard oxidic (i.e. entirely reduced in-situ) catalyst having the same Cu:Zn:Mg:Al molar ratio, tested under the same conditions. Measurements were taken at 17 hours on-line and 144 hours on-line. The results were as follows:

| Catalyst | Time on-line | Relative Activity |
| --- | --- | --- |
| Example 1a | 17 | 1.46 |
| Example 2c | 17 | 1.29 |
| Example 3b | 17 | 1.33 |
| Standard | 17 | 1.00 |
| Example 1a | 144 | 1.52 |
| Example 2c | 144 | 1.24 |
| Example 3b | 144 | 1.42 |
| Standard | 144 | 1.00 |

The results show superior activity and a lower rate of deactivation for the catalysts of the present invention compared to a standard oxidic catalysts of the same Cu:Zn:Mg:Al molar ratio.

Example 5

The Method of Example 1 was repeated except that the washed intimate mixture was dried in a pan drier at 110° C. for 6 hours in a static air oven rather than spray dried, prior to the drying at 210-240° C. The dried powder was reduced and passivated according to the method of Example 1. Again, the reduced and passivated powder was formed into cylindrical pellets with diameter 5.4 mm and length 3.2 mm and density about 2.0. The copper surface area was measured using the above method.

| Sample | Cu surface area ($m^2$/g Cu) |
| --- | --- |
| Example 5 | 84.4 |

A range of pellet densities was explored. The mean horizontal crush strengths were measured as described above.

| Sample | Pellet Density g/$cm^3$ | MHCS as made kg | MHCS Re-Reduced kg | MHCS Ratio |
| --- | --- | --- | --- | --- |
| Example 5a | 1.71 | 7.7 | 8.3 | 1.078:1 |
| Example 5b | 1.95 | 14.4 | 12.2 | 0.847:1 |

The residual strength of these catalysts following reduction is very high compared to the standard oxidic catalysts (reduced in-situ). The relative activity of Example 5b measured using the test described in Example 4, compared to the standard oxidic (reduced in-situ) catalyst at 144 hours was 1.73. Hence the activity of the catalyst of the present invention is considerably higher than the standard catalyst.

Example 6

Comparative

A catalyst was prepared according to Example 1 of U.S. Pat. No. 4,863,894 (with a molar ratio of Cu:Zn:Al of 59.8:25.6:14.5). The washed material was dried at 110° C. but without a drying step at 180-240° C., and then reduced using a mixture of 5% $H_2$+95% $N_2$ by volume. The reduced powder was passivated and shaped in the same way as Example 1. A range of pellet densities was explored. The MHCS was measured on the as-made pellet and on the pellet after re-reduction to simulate strength in-situ.

| Sample | Pellet Density (g/mL) | MHCS As-Made (kg) | MHCS Re-reduced (kg) | MHCS Ratio | Shrinkage on Reduction (% v/v) |
| --- | --- | --- | --- | --- | --- |
| Comparative 6a | 1.70 | 8.1 | 1.7 | 0.210:1 | 16.2 |
| Comparative 6b | 1.83 | 11.4 | 3.7 | 0.325:1 | 19.2 |
| Comparative 6c | 1.88 | 12.3 | 3.8 | 0.309:1 | 19.0 |

While the pelleted material is initially strong, the re-reduction figure shows considerable strength loss giving a strength ratio much lower than 0.500:1 and a shrinkage higher than both conventional oxidic catalysts and the present invention. High shrinkage is undesirable in catalysts as it is wasteful of reactor volume.

The catalyst (Example 6c) was tested according to the test method set out in Example 4. The relative activity of the catalyst fell to 0.97 at 144 hours.

Example 7

Testing—Low-Temperature Water-Gas Shift

The water-gas shift activities of Example 1a and a conventional oxidic catalyst with the same molar ratio of Cu:Zn:Mg:Al were assessed by crushing the pelleted material and charging approximately 0.5 g of 0.6-1.0 mm fraction material to a laboratory-scale reactor. The catalyst was reduced prior to testing with 2% $H_2$/$N_2$ mixture at 150 to 220° C. then cooled to the desired operating temperature. The reactor was operated using a standard LTS gas composition as follows:

| | Component | | | | |
| --- | --- | --- | --- | --- | --- |
| | CO | $CO_2$ | $H_2$ | $N_2$ | $H_2O$ |
| % volume | 2.67 | 10.67 | 36.67 | 16.67 | 33.33 |

The process was operated at 27 Barg and in the temperature range 205 to 250° C. Space velocity was 20,000 to 80,000 $h^{-1}$.

The exit gas was analysed using infra-red analysis and the condensate was collected and analysed by gas chromatography to determine the conversion of CO. The conversion was followed for each catalyst as a function of time on line and temperature. The conversion after 1 week was 41% for the Example 1a against 37% conversion for the comparative oxide-based catalyst (reduced in-situ) indicating an increase in activity. Under the conditions used, the catalyst of the present invention displayed a greater selectivity than the oxidic catalyst. There was less methanol generated, i.e. catalyst was more selective and this was seen in the further reaction products, e.g. propionic acid, which were reduced by about 20% wt compared to the oxidic catalyst. From the conversion profile, the catalyst of the present invention also illustrated improved resistance to sintering, i.e. a slower die off than the oxidic catalyst.

Example 8

Catalyst Preparation: Effect of Shape and Pellet Density

The catalyst preparation of Example 1 was repeated. The spray drier feed had a solids content of 30-35% wt. The spray drier settings were:
Inlet Temperature: 280-300° C.
Outlet temperature: 110-120° C.
Pump Pressure: 18-20 bar Residual moisture content of the spray-dried powder was <5%. 95% wt of the particles had a particle size 63-250 μm (microns). The spray-dried product was subjected to the same drying, reduction and passivation as Example 1.

The reduced and passivated powder was formed into:
a) highly-domed, 4-lobed/fluted cylindrical pellets with diameter 6.0 mm and total length 4.0 mm and a pellet density of about 1.82 g/cm³. The top and bottom dome height was 1.5 mm,
b) highly-domed, 4-lobed/fluted cylindrical pellets with diameter 6.0 mm and total length 4.0 mm and a pellet density of about 2.02 g/cm³. The top and bottom dome height was 1.0 mm, and
c) highly-domed, 4-lobed/fluted cylindrical pellets with diameter 5.0 mm and total length 4.0 mm and a pellet density of about 1.83 g/cm³. The top and bottom dome height was 0.5 mm.

The copper surface areas were measured using the above method.

| Example | Pellet Density g/cm³ | Copper surface area m²/g Cu |
|---|---|---|
| Example 8a | 1.82 | 75.8 |
| Example 8b | 2.02 | 73.7 |
| Example 8c | 1.83 | 78.3 |

The MHCS was determined on the pellets as made and also following a re-reduction to simulate the strength in-situ. The results were as follows.

| Sample | Pellet Density (g/mL) | MHCS As-Made (kg) | MHCS Re-reduced (kg) | MHCS Ratio | Shrinkage on Reduction (% v/v) |
|---|---|---|---|---|---|
| Example 8a | 1.82 | 7.0 | 4.0 | 0.571:1 | 8.9 |
| Example 8b | 2.02 | 8.1 | 4.6 | 0.568:1 | 9.7 |
| Example 8c | 1.83 | 12.1 | 9.1 | 0.752:1 | 9.6 |

The properties of the as-made pellets (crushed and sieved) were measured using nitrogen absorption as follows:

| Sample | BET SA (m²/g) | Pore Volume (cm³g⁻¹) |
|---|---|---|
| Example 8a | 107.1 | 0.26 |
| Example 8b | 114.4 | 0.29 |
| Example 8c | 91.5 | 0.25 |

The results show that a range of unique shaped catalyst pellets may be made with sufficient strength and surface area for large-scale industrial use.

Example 9

Testing—Low-Temperature Water-Gas Shift

Catalysts were prepared according to the method Example 1 in which the washing step was adjusted to manipulate the residual $K_2O$ content.

The spray-dried products were subjected to the same drying, reduction and passivation as Example 1. The reduced and passivated powders were formed into cylindrical pellets with diameter 5.4 mm and length 3.6 mm and a pellet density of about 1.8 to 2.0 g/cm³.

The WGS activity and selectivity of these catalysts and a conventional oxidic catalyst with the same molar ratio of Cu:Zn:Mg:Al were assessed using the method and apparatus of Example 6. The results after 1 week was as follows:

| Example | Alkali content ppm | Conversion % | Selectivity Ratio |
|---|---|---|---|
| Example 9a | 380 | 51.1 | 1.22 |
| Example 9b | 310 | 51.1 | 1.14 |
| Example 9c | 1154 | 38.5 | 2.20 |
| Example 9d | 1571 | 30.5 | 2.41 |
| Comparative Oxidic catalyst | 340 | 37.0 | 1.00 |

The results show that the catalysts of the present invention having a low (<500 ppm) alkali level are more active and have a superior selectivity than the conventional oxidic catalyst and that increasing the alkali level to ≥1000 ppm can give comparable activity with a significant enhancement in selectivity. Thus alkali levels between 0.1% wt and 0.2% wt may offer improved water gas shift selectivity.

The invention claimed is:
1. A catalyst suitable for use in carbon oxides conversion reactions in the form of a pellet formed by compression of a reduced and passivated catalyst powder, said catalyst powder comprising copper in the range 10-80% by weight, zinc oxide in the range 20-90% by weight, alumina in the range 5-60% by weight and optionally one or more oxidic promoter compounds selected from the group consisting of compounds of Mg, Cr, Mn, V, Ti, Zr, Ta, Mo, W, Si and rare earths in the range 0.01-10% by weight, wherein said pellet has a mean horizontal crush strength as made of ≥6.5 kg, a reduced to as-made mean horizontal crush strength ratio of ≥0.5:1, and a copper surface area determined by decomposition of nitrous oxide above 60 m²/g Cu.
2. A catalyst according to claim 1 wherein the catalyst powder comprises the one or more oxidic promoter compounds selected from the group consisting of compounds of

Mg, Cr, Mn, V, Ti, Zr, Ta, Mo, W, Si and rare earths in an amount in the range 0.01-10% by weight.

3. A catalyst according to claim 1 wherein the catalyst powder comprises magnesium in an amount 1-5% by weight, expressed as MgO.

4. A catalyst according to claim 1 wherein the weight ratio of Cu:Zn expressed as oxide is 1:1 or higher.

5. A catalyst according to claim 1 wherein the crush strength ratio is ≥0.600:1.

6. A catalyst according to claim 1 wherein the mean horizontal crush strength of the catalyst as made is ≥10.0 kg.

7. A catalyst according to claim 1 wherein the copper surface area is ≥70 m$^2$/g Cu.

8. A catalyst according to claim 1 wherein the catalyst is in the form of a flat-ended cylindrical pellet, ring or trilobe or a domed cylinder having two or more grooves running along its length, optionally with one or more holes extending there-through.

9. A catalyst according to claim 1 wherein the pellet has a density in the range of 1.4 to 2.5 g/cm$^3$.

10. A catalyst according to claim 1 wherein the crush strength ratio is ≥0.650:1.

11. A catalyst according to claim 1 wherein the crush strength ratio is ≥0.700:1.

12. A catalyst according to claim 1 wherein the crush strength ratio is ≥0.750:1.

13. A catalyst according to claim 1 wherein the mean horizontal crush strength of the catalyst as made is ≥12.0 kg.

14. A catalyst according to claim 1 wherein the copper surface area is ≥75 m$^2$/g Cu.

15. A catalyst according to claim 1 wherein the copper surface area is ≥80 m$^2$/g.

16. A catalyst according to claim 1 wherein the pellet has a density in the range 1.8 to 2.4 g/cm$^3$.

* * * * *